(12) United States Patent
Frazier

(10) Patent No.: US 7,607,965 B1
(45) Date of Patent: Oct. 27, 2009

(54) DISCREET INFANT FEEDING SYSTEM

(76) Inventor: Amelia June Frazier, 2881 Providence Way, Pomona, CA (US) 91767

( * ) Notice: Subject to any disclaimer, the term of this patent is extended or adjusted under 35 U.S.C. 154(b) by 50 days.

(21) Appl. No.: 12/198,851

(22) Filed: Aug. 26, 2008

(51) Int. Cl.
*A61M 1/06* (2006.01)
*A41C 3/04* (2006.01)

(52) U.S. Cl. .......................................... 450/36; 604/74

(58) Field of Classification Search ................... 450/36, 450/1; 2/104–106, 113–115, 69; 604/74–76, 604/343–346, 317; 119/14.12
See application file for complete search history.

(56) References Cited

U.S. PATENT DOCUMENTS

| | | | | |
|---|---|---|---|---|
| 163,022 | A * | 5/1875 | Marsch et al. | ................. 604/76 |
| 195,594 | A * | 9/1877 | Patch | ........................... 52/409 |
| 949,414 | A * | 2/1910 | Cunningham | ................ 604/76 |
| 5,601,605 | A | 2/1997 | Crowe et al. | |
| 6,197,044 | B1 | 3/2001 | Clayton | |
| 6,213,840 | B1 | 4/2001 | Han | |
| 6,379,327 | B2 | 4/2002 | Lundy | |
| 6,887,217 | B1 | 5/2005 | Logan | |
| 6,896,581 | B2 | 5/2005 | Otto | |
| 7,094,217 | B2 * | 8/2006 | Fialkoff | ........................ 604/74 |
| 2008/0045888 | A1 | 2/2008 | Edwards et al. | |

* cited by examiner

*Primary Examiner*—Gloria Hale
(74) *Attorney, Agent, or Firm*—Jafari Law Group, Inc.; David V. Jafari

(57) ABSTRACT

The invention is a system for discreet infant breastfeeding, which utilizes a device that may be concealed underneath a human female's articles of clothing and allows milk to flow directly from the feeding female's breast and to an artificial nipple that is placed in the infant's mouth for feeding purposes, said device configured so that a mother feeding her infant child does not need to expose herself when, for example, in public. In one embodiment of the present invention, an infant feeding device that allows mothers to breast-feed their infants directly without the use of a pump and in a private manner, comprises an artificial nipple including one or more openings for dispensing milk; and an elongated tubular body fluidly coupled to said one or more openings of said artificial nipple, including a receiving end adapted for attaching to the human female areola, in a manner so as to receive milk from said female.

17 Claims, 4 Drawing Sheets

DISCREET INFANT FEEDING SYSTEM

TECHNICAL FIELD OF THE INVENTION

The present invention relates in general to a system for discreet infant feeding that allows a mother to feed an infant directly in an efficient and concealed manner. More specifically, the invention relates to such devices that allow milk to flow directly from a mother's breast to a artificial nipple that is placed in the infant's mouth for feeding purposes, said device configured so that a mother feeding her infant child does not need to expose herself when, for example, in public.

COPYRIGHT & TRADEMARK NOTICE

A portion of the disclosure of this patent application may contain material that is subject to copyright protection. The owner has no objection to the facsimile reproduction by any one of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and shall not be construed as descriptive or to limit the scope of this invention to material associated only with such marks.

BACKGROUND OF THE INVENTION

It is believed by many physicians and mothers that breastfeeding an infant has various benefits. Some of these benefits may include protecting an infant against infection and viruses, aiding the infant's development process as well as preventing certain diseases such as leukemia, some cancers and juvenile diabetes. Despite the known benefits, however, many mothers find breastfeeding time consuming and inconvenient. Others are unable to nurse their infants because of a lack of privacy in public places.

In the past, breastfeeding systems have allowed mothers to pump their breast milk into a bottle that can be stored for later use. Said inventions require the mother to fully disrobe while she is pumping her breast milk. This requires a mother to seek a private location where she can disrobe comfortably. Said devices also require the mother to hold onto the apparatus and manually pump the breast milk, making it impossible for her to care for her child or perform other tasks at the same time.

Other devices have been designed using discreet pumps that allow the mother to move about freely while pumping her breast milk. Said devices include special elastic brassieres to help support the pump and bottle, leaving the mother's hands free to perform other tasks. However, these devices are uncomfortable and thus undesirable; furthermore, such devices provide discreet pumping but later require the mother to gather the milk from a receptacle, place it into a bottle and later feed her child—this process is time consuming and impractical.

Some devices comprise of a hands-free breast pump and bottle that are supported by elastic bras. Said bras are typically made of an elastic material with slits positioned over the nipple. These slits are used to hold and support the breast pump and bottle. Although said inventions a hands-free mechanism, they often require the mother to disrobe and wear a separate elastic bra with slits, solely for the purpose of pumping her breast milk. This too may be inconvenient for a mother who is in a public place or has to feed her infant in a timely manner.

Another example of other hands-free breastfeeding systems include a portable breast pumping system that comprises a breast receptor, body strap and a collection container for receiving the breast milk. The body strap is used to securely support the breast receptor and the collection container against the mother's body. While such devices allow the mother to move about freely while pumping her breast milk, it is too complicated and bulky for practical use. Such devices often utilize several other elements including, for example a waist belt, a refrigeration container, and a breast receptor support bra. Such extra elements may be costly and difficult to use. Such devices also allow breast milk to flow from the mother's breast into a container, not allowing the infant to be fed directly, which is often desirable for many mothers as a preferred practice of feeding their child.

There is a need in the art for a breastfeeding system that allows mothers to nurse their infants directly, rather than by a bottle. Specifically, there is a need for a device that is discreet and allows a mother to hold her infant or perform other tasks, rather than a pump, throughout the feeding process. There is also a need for a system that allows mothers to nurse their infants in public places without having to disrobe or change their brassieres. A simple system that is easy to use and convenient is necessary for mothers who need to nurse their infants quickly. It is to these ends that the present invention has been developed.

SUMMARY OF THE INVENTION

To minimize the limitations in the prior art, and to minimize other limitations that will be apparent upon reading and understanding the present specification, the present invention describes a system for discreet infant feeding, which utilizes a device that may be concealed underneath a mother's articles of clothing and allow milk to flow directly from a mother's breast and to a artificial nipple that is placed in the infant's mouth for feeding purposes, said device configured so that a mother feeding her infant child does not need to expose herself when, for example, in public.

An infant feeding device that allows mothers to breastfeed their infants directly without the use of a pump and in a private manner, in accordance with the present invention, comprises an artificial nipple including one or more openings for dispensing milk; and an elongated tubular body fluidly coupled to said one or more openings of said artificial nipple, including a receiving end adapted for attaching to a human female areola, in a manner so as to receive milk from said human female.

A system for breastfeeding an infant, in accordance with the present invention, comprises a nursing bra; a support cup, including openings to provide access to a human female areola, said support cup coupled to said nursing bra in a manner so that said support cup may be exposed to receive a feeding tube; and an artificial nipple including one or more openings for dispensing milk, wherein said feeding tube further comprises an elongated tubular body fluidly coupled to said one or more openings of said artificial nipple, including a receiving end adapted for attaching to said human female areola, in a manner so as to receive milk from said human female.

Another infant feeding system that allows mothers to breastfeed their infants directly through a discreet feeding device, in accordance with the present invention, comprises a nursing bra; a conical shaped support cup made of a flexible material that is worn under said nursing bra; an opening in said support cup that is positioned over a human female's areola, allowing said areola to be accessed through said opening during breastfeeding; a flexible funnel shaped component that is secured to said areola on one end and a flexible tubular body on a receiving end; an adhesive material that securely holds said flexible funnel shaped component to said support cup; and an artificial nipple that is fluidly coupled to said flexible tubular body, said artificial nipple including one or more openings for dispensing milk in a manner so as to receive milk from said human female.

It is an objective of the present invention to provide mothers who are nursing with a breastfeeding system that allows them to feed their infants directly, rather than with a bottle when they are in public places.

It is another objective of the present invention to allow mothers to comfortably breastfeed their infants in public places without having to disrobe or expose themselves.

Finally, it is yet another objective of the present invention to provide mothers with a discreet breastfeeding system that allows them to care for their infant or perform other tasks throughout the feeding process.

These and other advantages and features of the present invention are described herein with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

DETAILED DESCRIPTION OF THE DRAWINGS

In the following discussion that addresses a number of embodiments and applications of the present invention, reference is made to the accompanying drawings that form a part hereof, where depictions are made, by way of illustration, of specific embodiments in which the invention may be practiced. It is to be understood that other embodiments may be utilized and changes may be made without departing from the scope of the present invention.

In the present disclosure, the term milk refers to breast milk, particularly the milk produced by a human female, which may be fed to infants, toddlers, and young children by breastfeeding. It is known that breast milk may provide the primary source of nutrition for newborns before they are able to eat solid food and digest a wider variety of foods. In the present disclosure, the term milk may include, and in no way limiting the scope of the present invention, the initial milk produced by a female often referred to as colostrum, which is high in the immunoglobulin IgA, a component that coats the gastrointestinal tract. It is well known that this may help to protect the newborn until its own immune system is functioning properly along with creating a mild laxative effect, expelling meconium and helping to prevent the build up of bilirubin (a contributory factor in jaundice).

Similarly, the term infant child includes, without limiting the scope of the present invention, infants, toddlers, or young children that may be breast fed by a female human. Milk or breast milk, may also include foremilk, the milk released at the beginning of a feed, which is watery, low in fat and high in carbohydrates relative to the creamier hind milk, which is released as the feed progresses. Therefore, the term milk in the present disclosure is defined as any of the secretions from female mammary glands that may be fed to an infant, toddler, or young child, without limiting the scope of the present invention.

Figure 1:
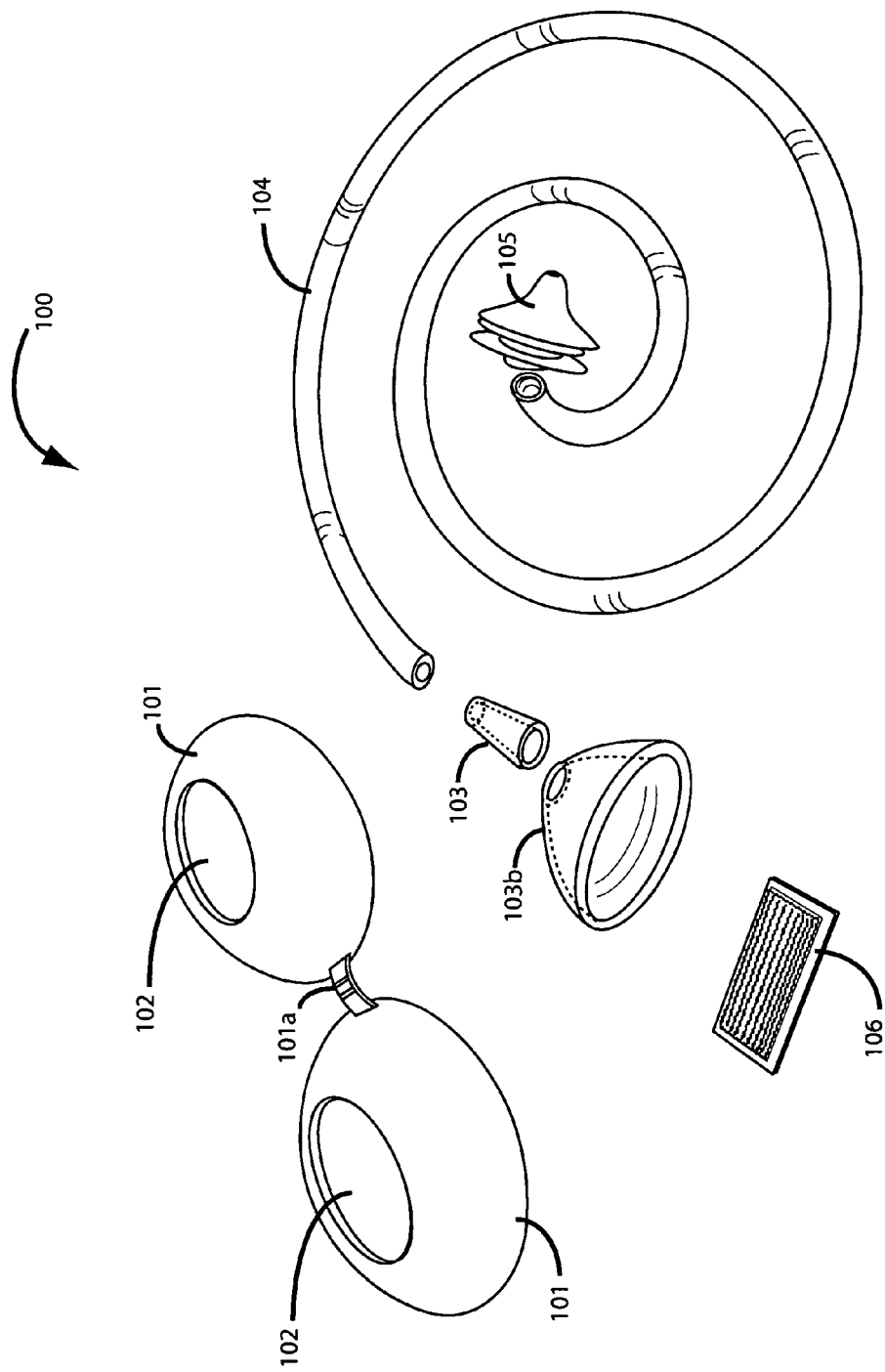
FIG. 1 illustrates system 100, comprising of plastic or gelatinous support cups with round cutouts, a funnel, a feeding tube and an artificial nipple, in accordance with one embodiment of the present invention.

Turning to the first figure, FIG. 1 illustrates an embodiment of the present invention. Specifically, FIG. 1 shows discreet feeding system 100 (system 100), comprising of support cups 101 with support cups connector 101a and openings 102, funnel 103, feeding tube 104, and artificial nipple 105.

Typically, system 100 is one in which support cups 101 are worn on the inside of the mother's brassiere. Support cups 101 may be made of any material that is typically used for support cups on regular bras without deviating from the scope of the present invention. In one embodiment support cups 101 may be made in a conical shape so as to conform to the shape of a female breast, constructed of a padded cotton or polyester material. In another embodiment, support cups 101 may be made in a conical shape so as to conform to the shape of a female breast, constructed of a gelatinous silicone material enclosed inside a fabric cover so as to add support and structure to support cups 101.

As shown, support cups 101 further include support cups connector 101a, which may be any known connector for female support cups known in the art, for example connector 101a may be one such as those connectors found in existing nursing bras. In one embodiment of the present invention, support cups 101 are part of a nursing bra and are not directly coupled with a connector such as connector 101a, but are rather held in place by said nursing bra. Such embodiment is further described in more detail below with reference to FIG. 2 and FIG. 3.

Openings 102 are typically cutouts that are positioned over a female's areola, allowing for easy access of her nipple during the breastfeeding process. Openings 102 may be constructed in any manner without deviating from the scope of the present invention. For example, in one embodiment, openings 102 are cut-outs shaped so as to allow access to a mother's nipple through support cups 101. In another embodiment, openings 102 are preformed during construction of support cups 101 such as by knitting or stitching methods.

Funnel 103 is typically a small funnel shaped component of system 100, which is large enough to snuggly fit over a mother's areola. In one embodiment, funnel 103 may comprise a flexible plastic or gelatinous material that may be comfortably coupled with the female's areola. In an exemplary embodiment (particularly shown in FIG. 1), funnel 103 is a smaller component adapted to couple with a human female's nipple, and includes a removable funnel component 103a adapted to fit snuggly around a human female's areola.

Funnel components 103 and 103a may be directly connected to, and an extension of an elongated tubular body or feeding tube 104, or may be removable components of system 100.

In an exemplary embodiment, funnel components 103 and 103a are removably coupled to an elongated tubular body, for example feeding tube 104, in a manner so that said components 103 and 103a may be either snapped on or otherwise mated with feeding tube 104 when utilizing system 100 to feed an infant. This may be desirable because such configuration allows for easy cleaning and thereby provides a more hygienic practice of system 100. Furthermore, such configuration may be desirable as a means of compartmentalizing system 100 into several parts thereby making system 100 more transportable by taking up less space, for example during travel or during storage.

Whether removable or directly attached to, or an extension of feeding tube 104, funnel 103 is inserted securely into openings 102 by way of an adhesive material such as materials that cause fabrics, yarns or fibers to stick together. For example and in no way limiting the scope of the present invention, such adhesive material may comprise a sticky adhesive, such as simply using an adhesive strip against one of support cups 101. Alternatively, in an exemplary embodiment, a loop and hook means such as Velcro™ may be utilized to securely hold funnel 103 and feeding tube 104 in place. In such embodiment, support cups 101 are made of a material to which a Velcro™ supportive component, such as Velcro™ strip component 106, may be utilized to properly hold funnel 103 and feeding tube 104 in place and connected to support cups 101.

Feeding tube 104 typically comprises an elongated tubular body made of a flexible, durable plastic material and fluidly coupled between an artificial nipple and a human female's breast (i.e. a human female's areola) in a manner so as to receive milk from the breast feeding female and dispense or provide said milk to an infant or child being breast fed via system 100. Feeding tube 104 may be constructed to be clear or to match a particular color. In an exemplary embodiment feeding tube 104 is a separate component from artificial nipple 105 and funnel 103 so that it may be removably coupled for cleaning and/or storage purposes, as described above; furthermore, in such exemplary embodiment feeding tube 104 is made of a flexible clear material, which is desirable during cleaning to make sure the device has been properly sanitized.

Artificial nipple 105 may be comprised of rubber, plastic, silicone, or any other material that is adaptable for use by an infant for feeding purposes, without limiting the scope of the present invention. Artificial nipple 105 may be directly connected to, attached to, an extension of feeding tube 104, or may be removably and fluidly coupled to feeding tube 104 for the practicalities associated with such configuration as described above (i.e. portable, and easy to sanitize). Artificial nipple 105 is naturally adapted to receive milk from a human female's breast (i.e. via an input end) and includes one or more output openings to dispense said milk for feeding.

Upon coupling all components of system 100 into a single unit, a mother may use system 100 in a concealed manner by placing support cups 101, snuggly and securely couple funnel 103 to her breast and areola (respectively), and run feeding tube coupled to funnel 103 underneath any article of clothing such as a blouse, a sweater, or any other article of clothing she may be wearing, thereby concealing system 100 underneath her clothes.

The only exposure of system 100 is artificial nipple 105 and a small portion of feeding tube 104. An example of said configuration is described below and discussed with reference to FIG. 4.

System 100 works in a manner such that the suction caused by an infant's suckling of artificial nipple 105 causes breast milk to flow through feeding tube 104, by way of funnel 103. The present invention may be used in both private and public places including restaurants, airports, offices or any other public or private premises.

Figure 2:
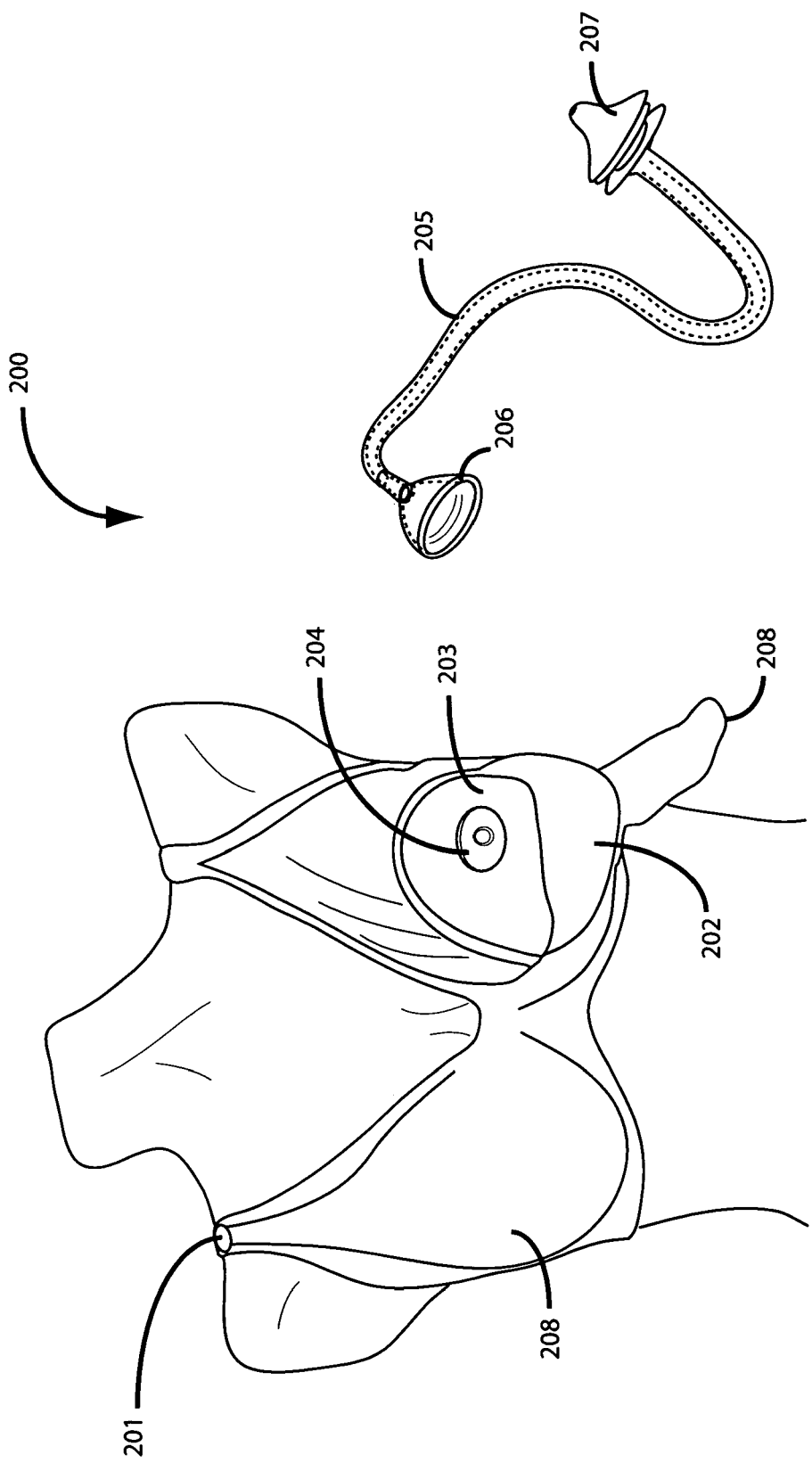
FIG. 2 illustrates system 200, demonstrating one configuration for the funnel and feeding tube to connect to the mother's breast, in accordance with an exemplary embodiment of the present invention.

Turning to the next figure, FIG. 2 illustrates system 200, demonstrating one configuration for the funnel and feeding tube to connect to the mother's breast, in accordance with an exemplary embodiment of the present invention. In said embodiment of the present invention shown in FIG. 2, system 200 comprises support cups 203, which are placed on the inside of nursing brassiere 201.

The shown embodiment shows a nursing bra or nursing brassiere that is typically worn and known to those skilled in the art. Thus, only a brief discussion of nursing brassiere 201 will be required for a more accurate and concise disclosure of the novel elements of the present invention.

Briefly, breast flap 202 of brassiere 201 is an internal flap accessible by pulling down an external component or external flap 208 of brassiere 201. Again, this configuration of a nursing brassiere is well known so as to provide a nursing woman with access to her breast when feeding her infant child. When used with system 200, nursing brassiere provides a nursing mother privacy and a discreet manner in which to breast feed her infant child.

In said embodiment, breast flap 202 of brassiere 201 is pulled down to expose support cup 203 and opening 204. In the present illustration it is possible to see that opening 204 is placed over a female's breast in a manner so as to provide access to her areola, enabling her to secure funnel 205 onto her breast, particularly her areola and nipple. This allows breast milk to flow from the breast to artificial nipple 207 by way of feeding tube 206.

Figure 3:
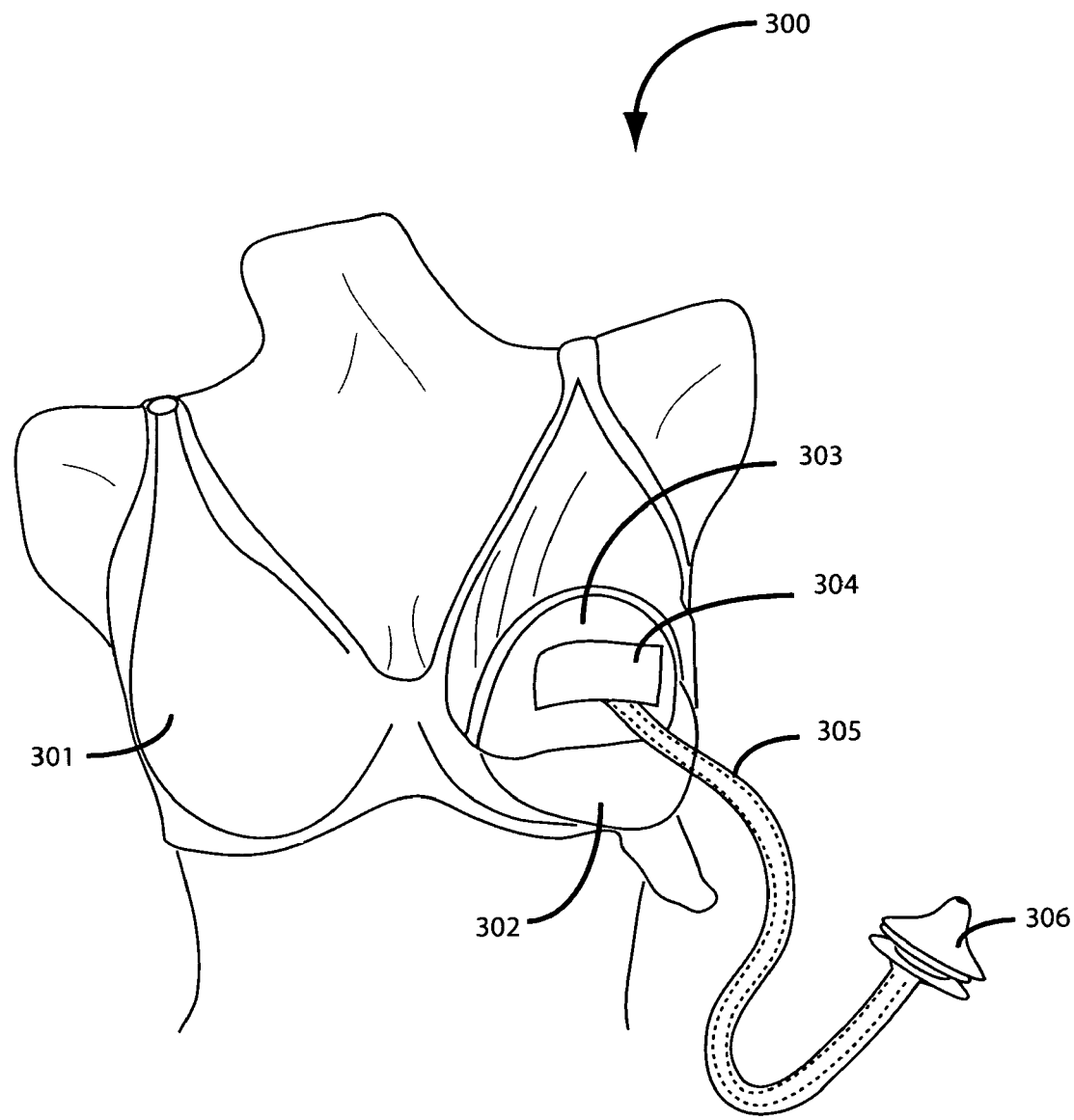
FIG. 3 illustrates another embodiment, specifically showing the manner in which the brassiere, support cups, funnel and feeding tube may be coupled and held securely in place against a human female's areola, in accordance with practice of the present invention.

Turning to the next figure, FIG. 3 illustrates another embodiment, specifically showing the manner in which the brassiere, support cups, funnel and feeding tube may be coupled and held securely in place against a mother's nipple, in accordance with practice of the present invention.

More specifically, FIG. 3 illustrates system 300 comprising a nursing brassiere 301 which includes a removable breast flap 302 and support cups 303 for each breast (only one shown exposed). Each of said support cups 303 further includes an opening (not shown since concealed in the present view), and is made of a soft fabric compatible with a loop and hook means such as a Velcro™ strip 304. In said embodiment, a funnel component coupled to feeding tube 305 may be securely fitted snuggly around a female's areola accessible through said openings of support cups 303. Strip 304 may therefore be securely attached to support cup 303 and prevent feeding tube 305 from being accidentally decoupled from the mother's breast.

Opening breast flap 302, and securing feeding tube 305 may be done discreetly and underneath a mother's articles of clothing without having to seek privacy or revealing herself to others around her. The only visible components of system 300 would be a portion of feeding tube 305, and of course artificial nipple 306. The next figure, particularly shows one embodiment of the present invention as it may appear when worn and utilized a mother to feed her infant child, while for example, in a public setting.

Figure 4:
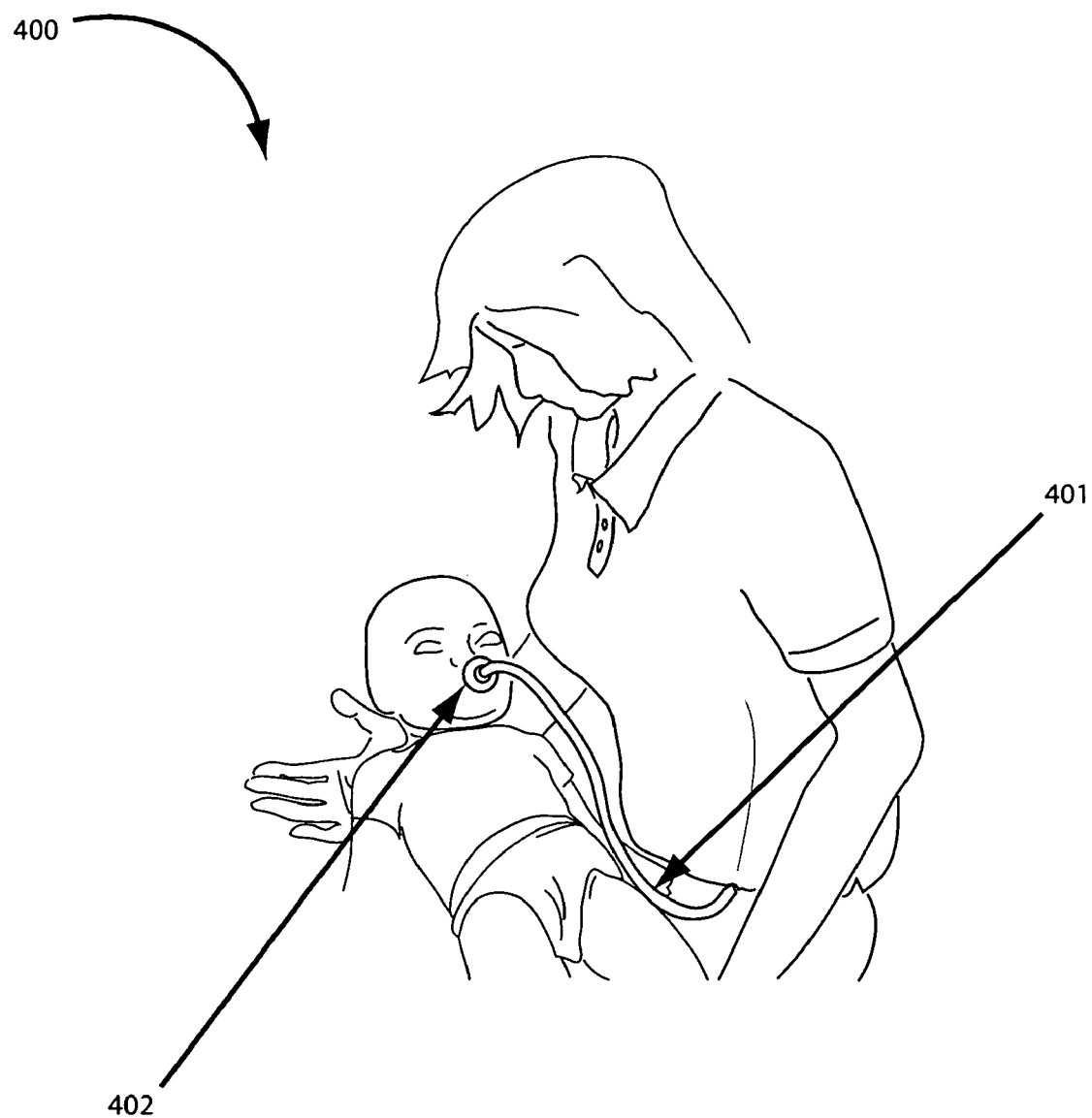
FIG. 4 illustrates an exemplary embodiment of the present invention, wherein a mother is able to directly breastfeed her infant in a public place in an efficient and concealed manner.

FIG. 4 illustrates an exemplary embodiment of the present invention, wherein a mother is able to directly feed her infant in a public place in an efficient and concealed manner.

More specifically, FIG. 4 illustrates system 400, comprising feeding tube 401 and artificial nipple 402; other components, which may be utilized with system 400, such as specialized support cups and bra, as described above, would be completely concealed underneath the mother's blouse.

As shown in the illustrated embodiment, flow tube 401 and artificial nipple 402 emerge from under the mother's blouse, allowing for an infant to be fed in a public place without requiring the mother to disrobe or to expose herself.

A discreet infant feeding system has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching. It is intended that the scope of the invention not be limited by this detailed description, but by the claims and the equivalents to the claims.

What is claimed is:

1. An infant feeding device that allows mothers to breastfeed their infants directly without the use of a pump and in a private manner, comprising:
   an artificial nipple including one or more openings for dispensing milk;
   an elongated tubular body fluidly coupled to said one or more openings of said artificial nipple, including a receiving end adapted for attaching to a funnel shaped component, wherein said funnel shaped component is adapted to couple with a human female areola, in a manner so as to receive milk from said human female;
   a support cup adapted with an opening configured to receive said funnel shaped component; and
   an adhesive material that securely holds said funnel shaped component to said support cup.

2. The device of claim 1, wherein said funnel shaped component is permanently coupled with said tubular body.

3. The device of claim 1, wherein said funnel shaped component is removably coupled with said tubular body.

4. The device of claim 1, wherein said support cup comprises a conical shape fitted to the shape of a woman's breast.

5. The device of claim 1, wherein said artificial nipple is permanently coupled with said tubular body.

6. The device of claim 1, wherein said artificial nipple is removably coupled with said tubular body.

7. A system for breastfeeding an infant, comprising:
   a nursing bra;
   a support cup, including openings to provide access to a human female areola, said support cup coupled to said nursing bra in a manner so that said support cup may be exposed to receive a feeding tube;
   an artificial nipple including one or more openings for dispensing milk, wherein said feeding tube further comprises an elongated tubular body fluidly coupled to said one or more openings of said artificial nipple, including a receiving end adapted for attaching to a funnel shaped component that is secured to said human female areola, in a manner so as to receive milk from said human female;
   an adhesive material applied to said support cup wherein said funnel shaped component is secured to said areola by way of the adhesive material applied to said support cup.

8. The system of claim 7, wherein said funnel shaped component is permanently coupled with said tubular body.

9. The system of claim 7, wherein said funnel shaped component is removably coupled to said tubular body.

10. The system of claim 7, wherein said adhesive material for securely coupling said funnel shaped component to said areola comprises a loop and hook strap.

11. The system of claim 10 wherein said support cup comprises a conical shape fitted to the shape of a woman's breast.

12. The system of claim 7, wherein said artificial nipple is removably coupled with said tubular body.

13. The system of claim 7, wherein said artificial nipple is permanently coupled with said tubular body.

14. The system of claim 7, wherein said adhesive material for securely coupling said funnel shaped component to said areola comprises a glue type adhesive.

15. An infant feeding device that allows mothers to breastfeed their infants directly through a discreet feeding device comprising:
   a nursing bra;
   a conical shaped support cup made of a flexible material that is worn under said nursing bra;
   an opening in said support cup that is positioned over a human female's areola, allowing said areola to be accessed through said opening during breastfeeding;
   a funnel shaped component that is secured to said areola on one end and a flexible tubular body on a receiving end;
   an adhesive material that securely holds said funnel shaped component to said support cup; and
   an artificial nipple that is fluidly coupled to said flexible tubular body, said artificial nipple including one or more openings for dispensing milk in a manner so as to receive milk from said human female.

16. The device of claim 15, wherein said adhesive material for securely holding said flexible funnel shaped component to said support cup comprises a loop and hook strap.

17. The device of claim 15, wherein said adhesive material for securely holding said flexible funnel shaped component to said support cup comprises a glue type adhesive.

* * * * *